(12) United States Patent
Newman et al.

(10) Patent No.: US 8,513,623 B2
(45) Date of Patent: Aug. 20, 2013

(54) INSTALLATION FOR STERILIZING OBJECTS BY MEANS OF A RADIATION SOURCE

(75) Inventors: John Thomas Newman, Thornton, CO (US); Volker Sigwarth, Sisseln (CH); Paul Alexander Smith, Los Alamos, NM (US)

(73) Assignee: Skan AG, Allschwil (CH)

( * ) Notice: Subject to any disclaimer, the term of this patent is extended or adjusted under 35 U.S.C. 154(b) by 610 days.

(21) Appl. No.: 12/514,166

(22) PCT Filed: Nov. 8, 2007

(86) PCT No.: PCT/CH2007/000550
§ 371 (c)(1),
(2), (4) Date: Apr. 5, 2010

(87) PCT Pub. No.: WO2008/055375
PCT Pub. Date: May 15, 2008

(65) Prior Publication Data
US 2012/0168642 A1    Jul. 5, 2012

Related U.S. Application Data

(60) Provisional application No. 60/857,569, filed on Nov. 8, 2006.

(51) Int. Cl.
*A61L 2/08*    (2006.01)
*G21K 5/10*    (2006.01)

(52) U.S. Cl.
CPC .... *A61L 2/08* (2013.01); *G21K 5/10* (2013.01)
USPC .................................................. 250/455.11

(58) Field of Classification Search
USPC ................ 250/492.3, 455.11; 198/419.1
See application file for complete search history.

(56) References Cited

U.S. PATENT DOCUMENTS 5,457,269 A * 10/1995 Schonberg .................... 588/305
5,740,221 A * 4/1998 Norman et al. ................. 378/58
(Continued)

FOREIGN PATENT DOCUMENTS

DE    10 73 388 B    1/1960
DE    33 21 195 A1    12/1984
(Continued)

OTHER PUBLICATIONS

International Preliminary Report on Patentability issued in connection with International Patent Appln. No. PCT/CH2007/000550.
Internataional Search Report, mailed Apr. 15, 2008, issued in connection with International Patent Appln. No. PCT/CH2007/000550.

*Primary Examiner* — Jack Berman
*Assistant Examiner* — Eliza Osenbaugh-Stewart
(74) *Attorney, Agent, or Firm* — McCarter & English, LLP (57) ABSTRACT

Disclosed is an installation (1) for sterilizing objects (8) by means of a radiation source (50). The installation (1) comprises an irradiation zone (5) in which the radiation source (50) is arranged. An entry zone (3), which is preceded by a feed zone (2), is mounted in front of the irradiation zone (5) while an exit zone (4), which is followed by a subsequent processing zone (9), is mounted behind the irradiation zone (5). A transportation line (6) that is used for conveying the objects (8) extends through the installation (1). One respective shield (7) is associated with the entry zone (3) and the exit zone (4). The entry zone (3) encompasses a first inlet opening (31) that has a passage to the feed zone (2) as well as a second inlet opening (32) which has a passage to the irradiation zone (5). The exit zone (4) has a first outlet (41) that has a passage to the irradiation zone (5) as well as a second outlet opening (42) which has a passage to the subsequent processing zone (9). The transportation line (6) extends in alignment through all inlet openings and outlet openings (31,32;41,42). The shields (7) are movable. In each position of the shields (7) in which the objects (8) that are conveyed through the installation (1) can penetrate one of the two inlet openings (31,32) or one of the two outlet openings (41,42), the other inlet opening (32,31) and the other outlet opening (42,41) are covered by the associated shield (7).

4 Claims, 10 Drawing Sheets

(56) References Cited

U.S. PATENT DOCUMENTS

| | | | |
|---|---|---|---|
| 6,291,003 B1 * | 9/2001 | Riemann et al. | 426/511 |
| 6,713,741 B2 * | 3/2004 | Miller | 219/700 |
| 7,459,706 B2 * | 12/2008 | Fontcuberta et al. | 250/492.3 |
| 7,753,977 B2 * | 7/2010 | Lyons et al. | 55/385.1 |
| 2006/0186350 A1 | 8/2006 | Fontcuberta et al. | |

FOREIGN PATENT DOCUMENTS

| | | |
|---|---|---|
| DE | 39 11 749 A1 | 10/1989 |
| EP | 0 570 946 A | 11/1993 |
| WO | WO 2006/111681 A2 | 10/2006 |

\* cited by examiner

INSTALLATION FOR STERILIZING OBJECTS BY MEANS OF A RADIATION SOURCE

FIELD OF THE INVENTION

The present invention relates to an installation for sterilizing objects by means of a radiation source for generating X-ray, gamma or electron radiation, as is used, for example, in industry for the manufacture of medical single-use articles. Such an installation first of all has an irradiation zone, in which the radiation source is arranged. An entry zone is in front of the irradiation zone, and a feed zone for loading the installation with the objects to be treated is in front of said entry zone. An exit zone adjoins the irradiation zone and said exit zone is followed by a subsequent processing zone in which the irradiated objects are output for the subsequent manufacturing process which occurs here. The subsequent processing zone is typically furnished as an isolator or clean room, in which people can be active. Objects to be treated are, for example, containers with a multiplicity of initially empty injection syringes, in which the containers are to be sterilized on the outside in the installation and are filled in the subsequent processing zone. A transportation line which is used to convey the objects passes through the installation. The transportation line is formed by, for example, a conveyor belt. A shield is respectively assigned to the entry zone and the exit zone in order to protect the people located in the vicinity of the installation.

PRIOR ART

Installations for beam sterilization, in which the transportation line is designed in a meandering form in the horizontal plane, are known from experience. The radiation source is positioned in a section lying behind curves, with shields being set-up along the transportation line, which shields attenuate the radiation with each deflection so that radiation which is harmful to people is no longer emitted at the loading and unloading openings of the transportation line, which are open to the outside.

WO 2006/111681 A2 discloses an installation for beam sterilization, in which the transportation line is designed in the vertical plane with in each case one step at a horizontally aligned rotary disk. The radiation source lies between the rotary disks and hence is shielded by the latter. The already disclosed installations require a complicated transportation system which moreover generates not insignificant amounts of abrasion as a result of the movement process, which abrasion, as contamination in the installation, must be removed. It becomes more likely that the objects to be treated do not remain in their predetermined position on the transportation line, but rather get stuck or fall off. Finally, curved or stepped transportation lines require more time for the objects to be treated to pass through and need an increased spatial requirement for the entire installation.

OBJECT OF THE INVENTION

Given the disadvantages of already known installations, the invention is based on the object of simplifying the conveying of the objects to be treated in the installation and at the same time strictly ensuring radiation safety. A further object consists of achieving a qualified class of cleanliness in the installation, at least from the radiation source up to and including the exit zone. Another object is to design the cladding of the installation to be more mounting and maintenance friendly. Furthermore, it is an object to propose a solution for the sealing of openings on the transportation line, e.g. during the decontamination cycle. Finally, it is an object to efficiently remove the undesired gasses, such as ozone in particular, created at the radiation source from the installation or to at least minimize the creation of such gasses.

SUMMARY OF THE INVENTION

The installation for sterilizing objects by means of a radiation source first of all has an irradiation zone in which the radiation source is arranged. In front of the irradiation zone there is an entry zone, which in turn is preceded by a feed zone. Adjoining the irradiation zone there is an exit zone which is followed by a subsequent processing zone. A transportation line which is used to convey the objects passes through the installation. In each case, a shield is assigned to the entry zone and the exit zone. The entry zone has a first inlet opening with a passage to the feed zone and a second inlet opening with a passage to the irradiation zone. The exit zone has a first outlet opening with a passage to the irradiation zone and a second outlet opening with a passage to the subsequent processing zone. The transportation line extends flush through the first inlet opening, the second inlet opening, the first outlet opening and the second outlet opening. The shields are movable and in every situation with regard to position of the shields in which one of the two inlet openings or one of the two outlet openings permits the passage of the objects transported through the installation, the other inlet opening and the other outlet opening are covered by the respectively assigned shield.

The following features relate to special embodiments of the invention: in one alternative, one shield is composed of two disk-shaped, rotatable elements, a connection extending between the two. The elements have material regions and cut-outs which are offset with respect to each other and do not overlap. The elements are arranged at a distance which allows an object to be held between the former. The shield is connected to a drive. One element has two cut-outs on its circumference, which cut-outs are open in the radial direction and are offset by 180° with respect to one another. Alternatively, the element has one cut-out, whose arc is a multiple of the size of the object and thus permits the latter's passage when the shield is moved.

In another alternative, one shield is composed of two plate-shaped, displaceable or pivotable elements, a connection extending between the two. The elements have material regions but no cut-outs and are arranged at a distance which allows an object to be held between the former. The shield in this alternative is also connected to a drive.

An air distributor in the form of a filter or a diffuser for generating a unidirectional air flow and a decontamination unit are available in the exit zone. Advantageously, a feed air filter and an exhaust air filter are also arranged in the exit zone.

The radiation source acts into a channel through which the transportation line for conveying the objects passes and which firstly extends to the second inlet opening of the entry zone and secondly extends to the first outlet opening of the exit zone. A feed air filter opens into the channel between the first outlet opening and the radiation source. An exhaust air line leads off the channel between the radiation source and the second inlet opening. Alternatively, this exhaust air line can lead off the entry zone.

A seal which can be activated is arranged on the second inlet opening in the entry zone with a passage to the irradiation zone, which seal is mounted on a fixed part of the installation and, when activated, seals the second inlet opening against the second element of the shield assigned to the entry zone. Alternatively, the seal can be mounted on the second element of the shield assigned to the entry zone and, when activated, seals the second inlet opening against a fixed part of the installation.

The housing of the sterilizing installation is manufactured from sandwich elements which adjoin one another and are sealed off against one another. A sandwich element has a radiation absorbing inner layer, preferably composed of lead, between two outer layers, preferably composed of a stainless steel plate. A seal is provided between adjacently arranged sandwich elements.

The treatment space acted upon by the radiation source is filled with an inert gas in order to at least minimize the creation of undesired gasses, such as in particular ozone.

EXEMPLARY EMBODIMENT

The detailed description of an exemplary embodiment of the installation for sterilizing objects by means of a radiation source follows below with reference to the appended drawings. Alternative solutions for the shield used in the installation are presented and, moreover, advantageous design details are disclosed in addition to the essential features.

The following provision applies for the entire description that follows: if reference numbers are contained in a figure for the purposes of unambiguity in the drawing but are not referred to in the directly associated text of the description, reference is made to their mentioning in preceding descriptions of figures. In the interest of clarity, the repeated labeling of components in subsequent figures is generally refrained from, as long as the drawing makes it clear without ambiguity that they are "recurring" components.

Figure 1A:
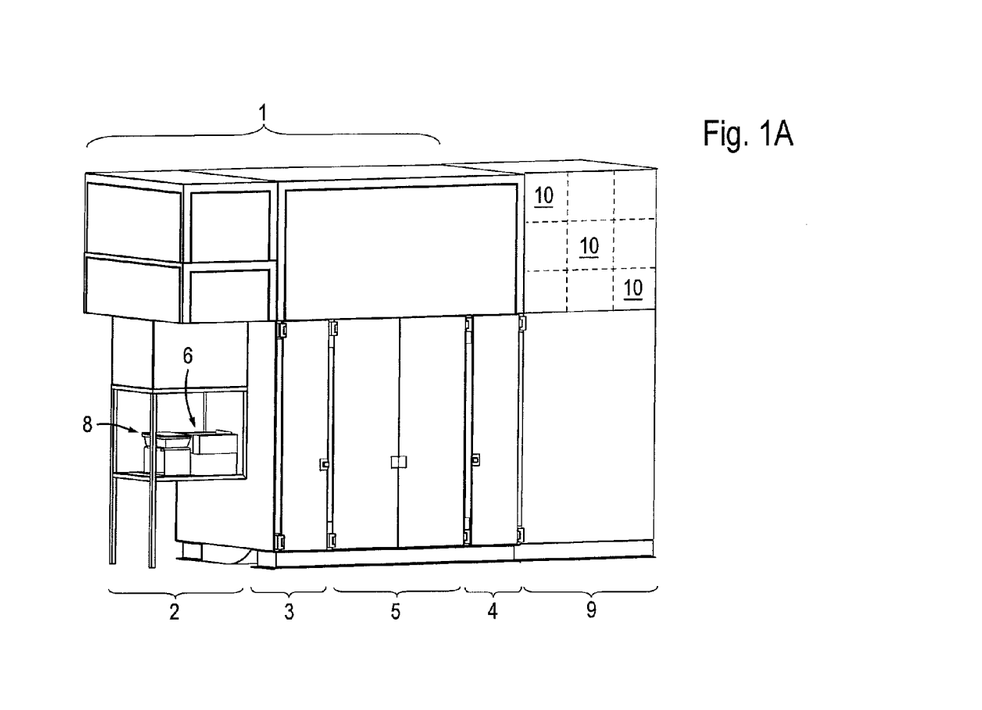
FIG. 1A—shows the design of an installation for sterilizing objects by means of a radiation source with an adjoining subsequent processing zone, in a perspective view.
Figure 1B:
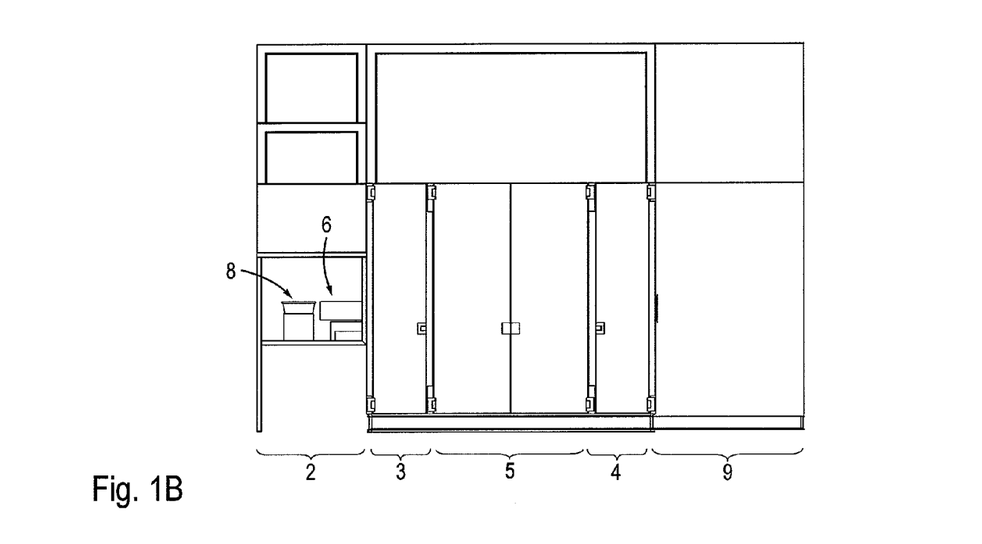
FIG. 1B—shows the design in accordance with FIG. 1A, in a frontal view.
Figure 2A:
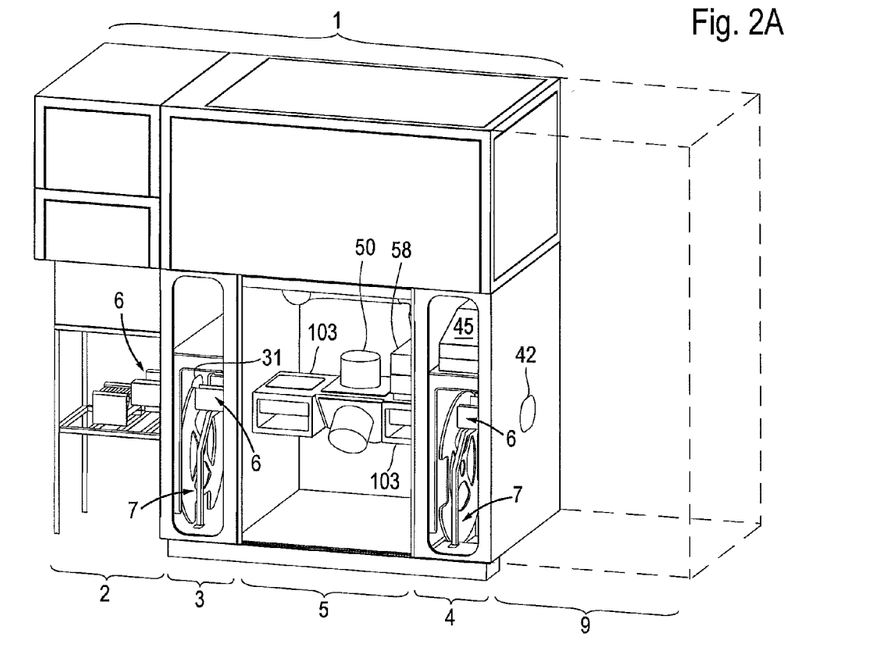
FIG. 2A—shows the design in accordance with FIG. 1A, with a partial view of the interior of the installation.
Figure 2B:
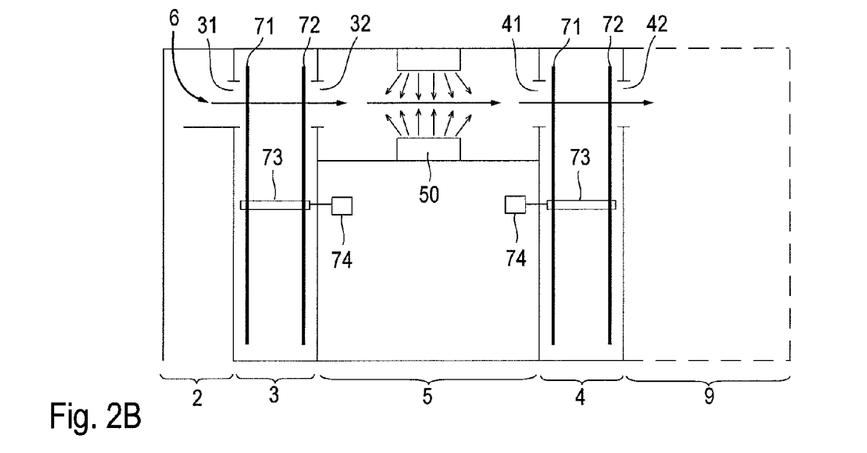
FIG. 2B—shows the design in accordance with FIG. 1A, in a schematic diagram.
Figure 3A:
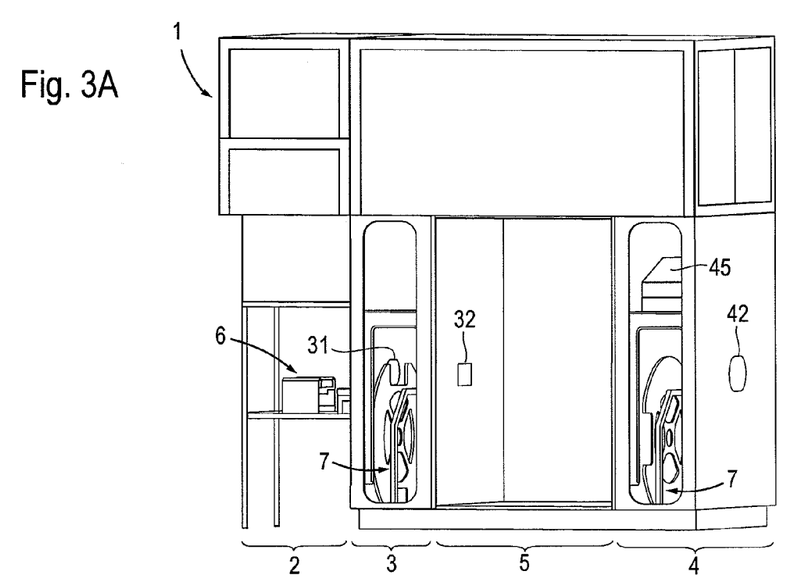
FIG. 3A—shows the design in accordance with FIG. 1A, without fixtures in the irradiation zone and without the subsequent processing zone, in a perspective view.
Figure 3B:
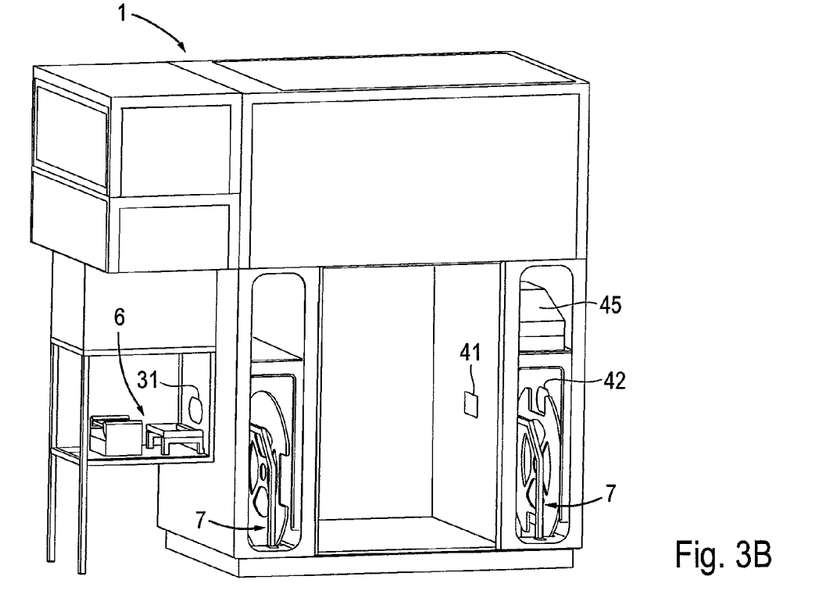
FIG. 3B—shows the design in accordance with FIG. 3A, from a different perspective.
Figure 10:
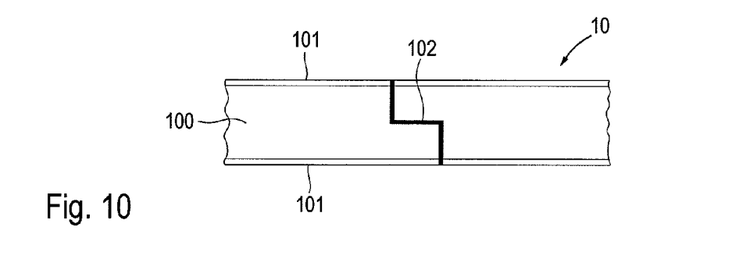
FIG. 10—shows two adjoining sandwich elements with a seal placed between them, in a schematic diagram.

FIGS. 1A, 1B and 10

An irradiation zone 5 forms the center of the installation 1, said zone being preceded by an entry zone 3 and followed by an exit zone 4. In front of the entry zone 3 there is a feed zone 2, in which the transportation line 6 to convey the objects 8 to be treated in the installation 1 starts. Here, the installation 1 is loaded with the objects 8 and the treated objects 8 are output at the end of the exit zone 4 in order to be subject to the continued manufacturing process in the subsequent processing zone 9. The exit zone 4 is adjoined by a subsequent processing zone 9, typically furnished as isolator or clean room, in which people can be active. Such objects 8 are, for example, containers with a multiplicity of initially empty injection syringes, in which the containers are to be sterilized on the outside in the installation and are filled in the subsequent processing zone 9.

The housing of the installation 1 is advantageously constructed from a multiplicity of sandwich elements 10. A sandwich element 10 has on its inside a thicker radiation absorbing layer 100—conventionally composed of lead—which lies between two outer layers 101 which, for example, are composed of a stainless steel plate. Seals 102 are inserted between adjoining sandwich elements 10.

FIGS. 2A to 3B

The transportation line 6 begins in the feed zone 2 and extends flush through the entire installation 1, that is to say the entry zone 3, the irradiation zone 5, and the exit zone 4. Within the irradiation zone 5, the transportation line 6 is surrounded by the channel 103, around which the radiation source 50, preferably in the form of an electron emitter, is arranged. The radiation source 50 acts on the objects 8 passing through the channel 103 on the transportation line 6. A shield 7 is installed in the entry zone 3 and exit zone 4, respectively. A feed air filter 58 connected to the channel 103 is located between the radiation source 50 and the transition to the exit zone 4. An air distributor 45 in the form of a filter or diffuser is provided in the exit zone 4.

The entry zone 3 has a first inlet opening 31 with a passage to the feed zone 2 and a second inlet opening 32 with a passage to the irradiation zone 5. The exit zone 4 has a first outlet opening 41 with a passage to the irradiation zone 5 and a second outlet opening 42 with a passage to the subsequent processing zone 9. The transportation line 6 extends flush through the four openings 31,32;41,42. In a first embodiment, the shield 7 has two disk-shaped, rotatable elements 71,72, between which there is a connection 73 which is similar to an axle. A drive 74 acts on the shield 7. The elements 71,72 extend past the four openings 31,32;41,42 to the extent that in certain situations with regard to positions these openings 31,32;41,42 are covered. In the illustrated embodiment, both elements 71,72 are positioned within the entry zone 3 or exit zone 4. Alternatively, the first element 71 could be placed in the feed zone 2 on the first inlet opening 31 and/or the second element 72 could be placed in the irradiation zone 5 on the second inlet opening 32.

FIGS. 4, 6A to 7C, 9A and 9B

Figure 4:
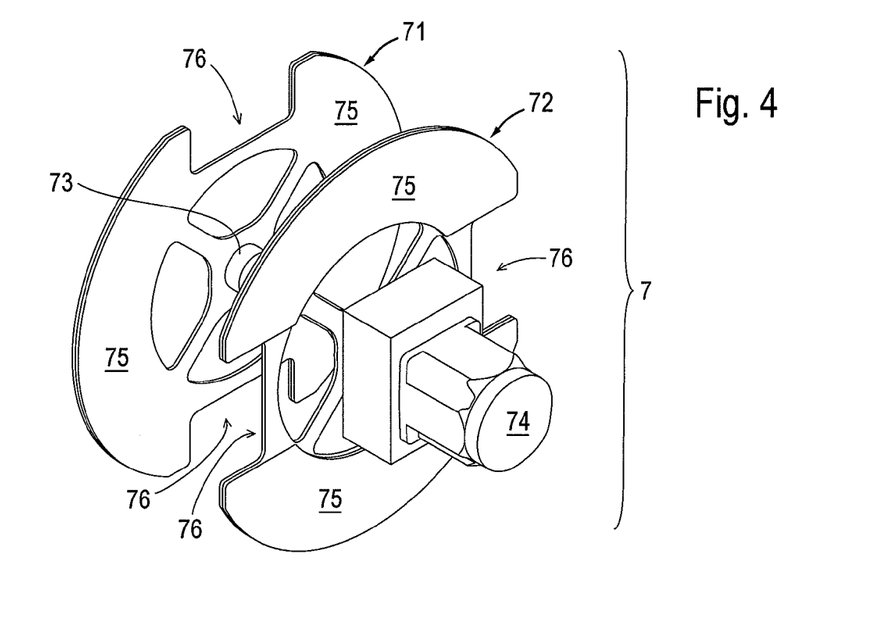
FIG. 4—shows a first embodiment of a shield from FIG. 2A, in a perspective view.
Figure 6A:
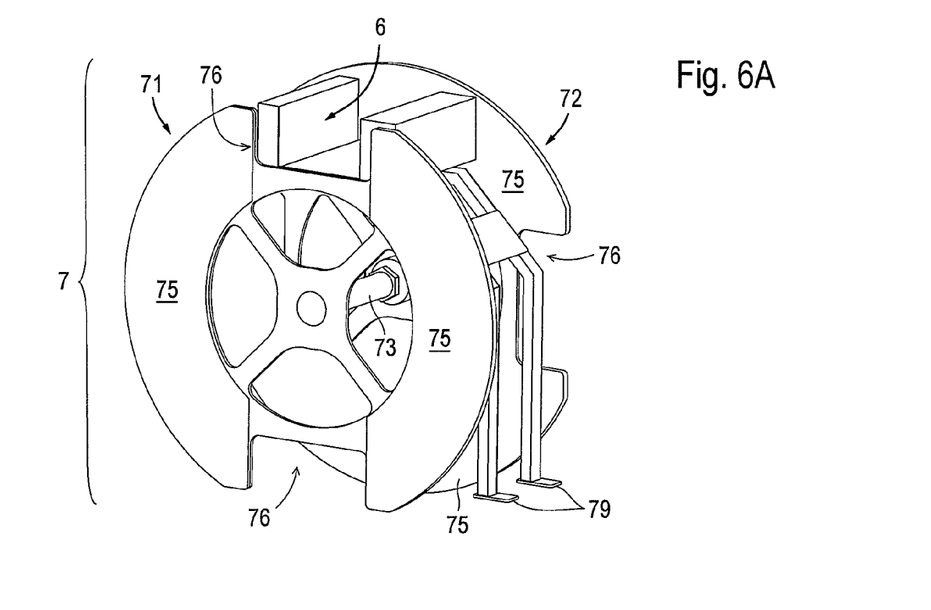
FIG. 6A—shows the shield in accordance with FIG. 4 with a section of a transportation line and a frame, in a perspective view.
Figure 6B:
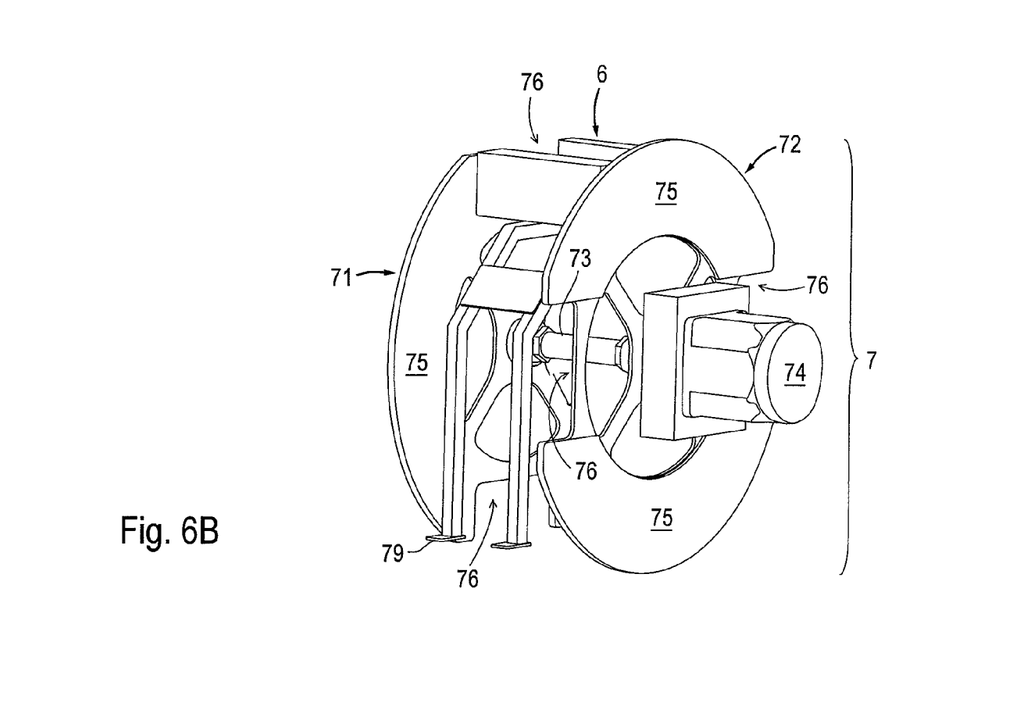
FIG. 6B—shows the design in accordance with FIG. 6A, from a different perspective.

In principle, the shield 7 has two disk-shaped elements 71,72, which are spaced parallel to one another in a congruent form and between which there is an axial connection 73. On its circumference, each element 71,72 has two cut-outs 76 which are open radially and offset by 180° with respect to one another. There are material regions 75 in the remainder of the annulus, while there are large-area apertures toward the center which serve to reduce weight. In accordance with the function of the shield 7 as a protection from the electron flow emitted by the radiation source 50, the elements 71,72 have a radiation-absorbing design with a layer composed of lead. The cut-outs 76 of the first element 71 are offset compared to the cut-outs 76 of the second element 72 to the extent that there is no overlap. The span of the cut-outs 76 must permit the objects 8 to pass through, and the clear distance between the elements 71,72 must be dimensioned in order to be able to hold a section of the transportation line 6 and an object 8 in the latter. A frame 79 serves to support the shield 7 installed in the installation 1. The drive 74 coupled to the shield 7 is preferably an electric motor. This embodiment of the shield 7 is provided for incremental continued rotation.

Figure 7A:
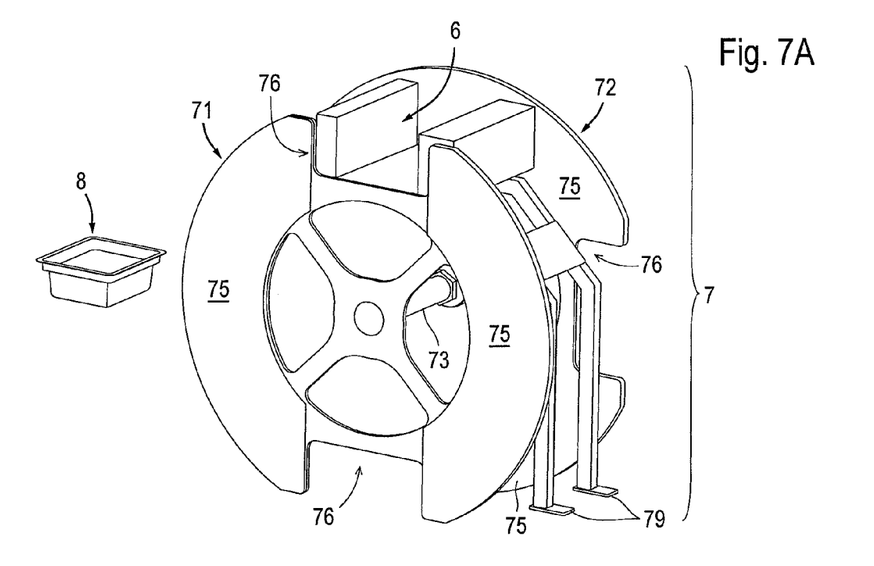
FIG. 7A—shows the design in accordance with FIG. 6A with an object to be treated which has approached, in a perspective view.
Figure 7B:
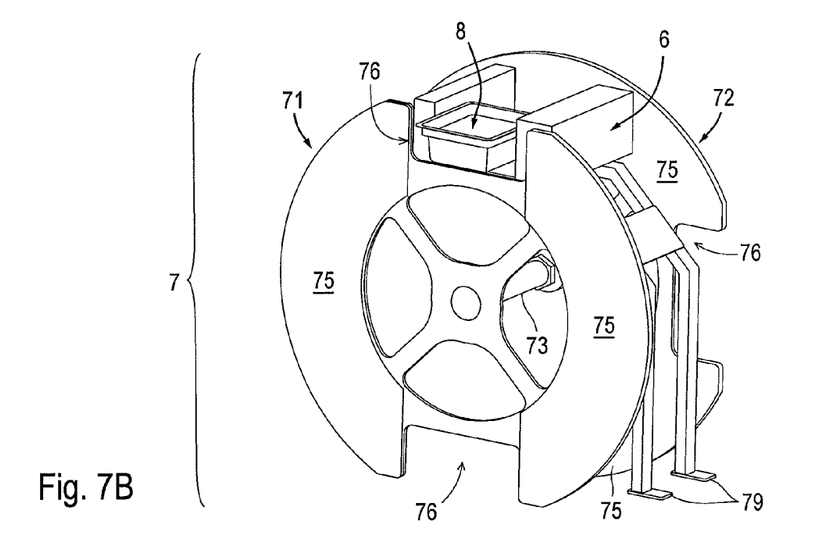
FIG. 7B—shows the design in accordance with FIG. 7A with an object brought within the shield on the transportation line, in a perspective view.
Figure 7C:
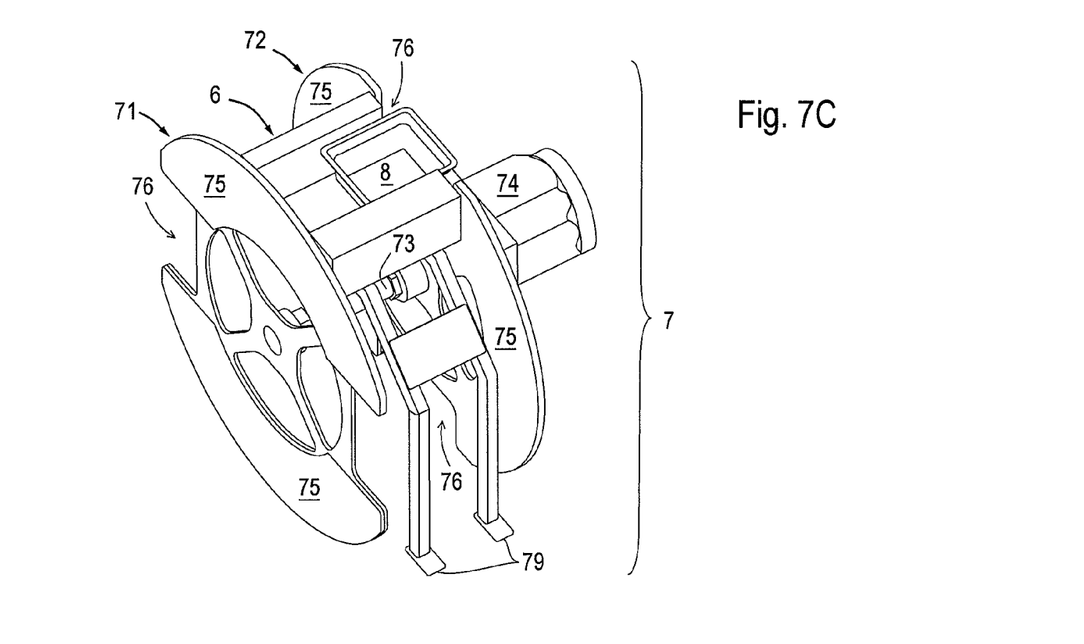
FIG. 7C—shows the design in accordance with FIG. 7A with an object leaving the shield via the transportation line, in a perspective view.

In a position of the shield 7 in which a cut-out 76 comes to rest on the passage of the transportation line 6, an object 8 can be inserted between the elements 71,72, or, on the other hand, can be unloaded. Insertion is effected through the first inlet opening 31 or the first outlet opening 41. Unloading is effected through the second outlet opening 32 or the second outlet opening 42. However, if a material region 75 is in front of the passage of the transportation line 6, that is to say in front of one of the openings 31,32;41,42 in the installation 1, the insertion or unloading of an object 8 is blocked in order to prevent radiation from passing through.

The adjustment between the shield 7 installed in the entry zone 3 and the shield 7 positioned in the exit zone 4 will be coordinated depending on the conceptual design of the processing passage of the object 8 to be treated through the installation 1.

Figure 9A:
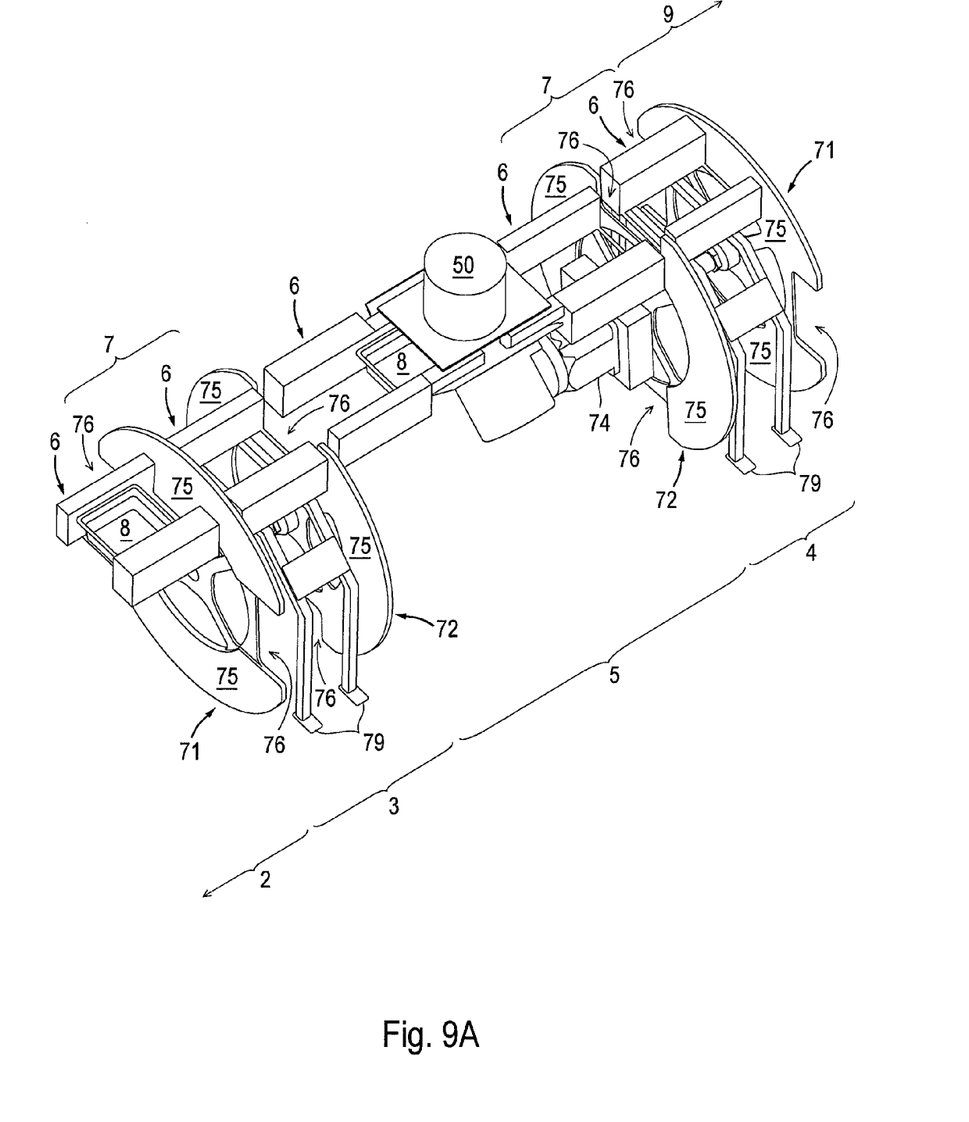
FIG. 9A—shows a characteristic situation with regard to position of the shields and the objects to be treated within the installation, in a schematic diagram.

In the situation with regard to position in accordance with FIG. 9A:

the passage between the feed zone 2 and the entry zone 3 via the first entry opening 31 is locked as a result of the material region 75 present; an object 8 is located in front of the entry zone 3;

the passage between the entry zone 3 and the irradiation zone 5 via the second entry opening 32 is open as a result of the cut-out 76 present; an object 8 has left the entry zone 3 and passes through the irradiation zone 5;

the passage between the irradiation zone 5 and the exit zone 4 via the first outlet opening 41 is open as a result of the cut-out 76 present; the entry of the object 8 into the exit zone 4 is clear; and the passage between the exit zone 4 and the subsequent processing zone 9 via the second outlet opening 42 is locked as a result of the material region 75 present.

This ensures that in each situation with regard to position of the advantageously flush transportation line 6 with the correspondingly arranged openings 31,32;41,42, the path for the radiation emitted by the radiation source 5 is never open to the outside in any direction along the transportation line 6. Thus, it is impossible to endanger people located in the vicinity of the installation 1.

Figure 9B:
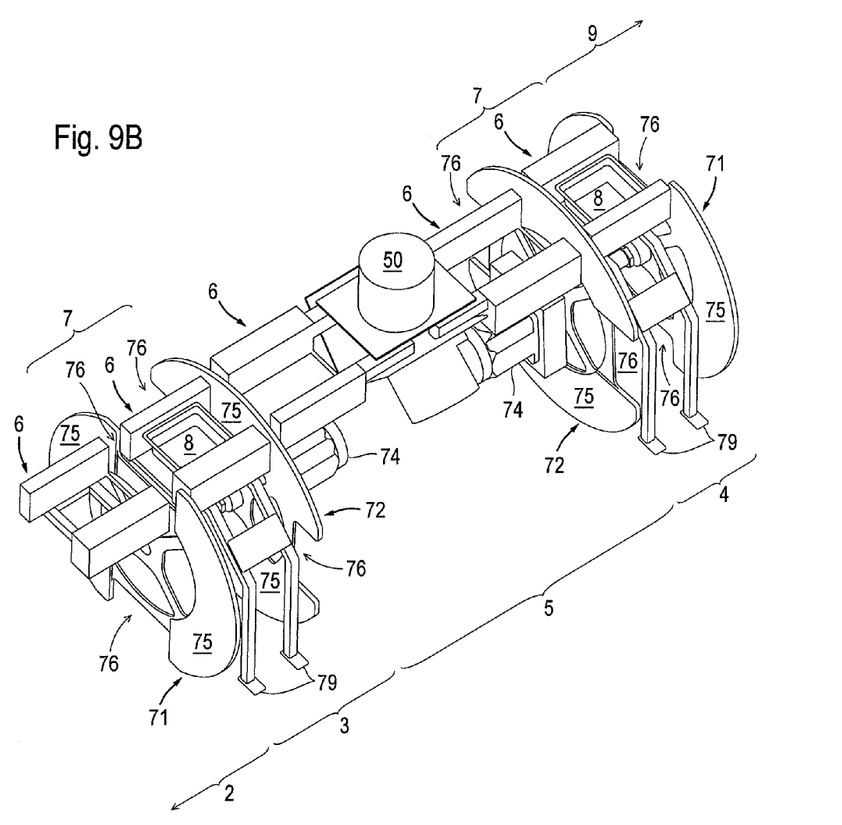
FIG. 9B—shows a further characteristic situation with regard to position of the shields and the objects to be treated within the installation, in a schematic diagram.

In the changed situation with regard to position in accordance with FIG. 9B:

the passage between the feed zone 2 and the entry zone 3 via the first inlet opening 31 is open as a result of the cut-out 76 present; an object 8 has passed from the feed zone 2 into the entry zone 3;

the passage between the entry zone 3 and the irradiation zone 5 via the second inlet opening 32 is locked as a result of the material region 75 present; the object 8 cannot leave the entry zone 3;

the passage between the irradiation zone 5 and the exit zone 4 via the first outlet opening 41 is locked as a result of the material region 75 present; and the passage between the exit zone 4 and the subsequent processing zone 9 via the second outlet opening 42 is open as a result of the cut-out 76 present; the object 8 can leave the exit zone 4 toward the subsequent processing zone 9.

This case also ensures that the emitted radiation cannot escape to the outside in any direction along the transportation line 6.

Figure 5:
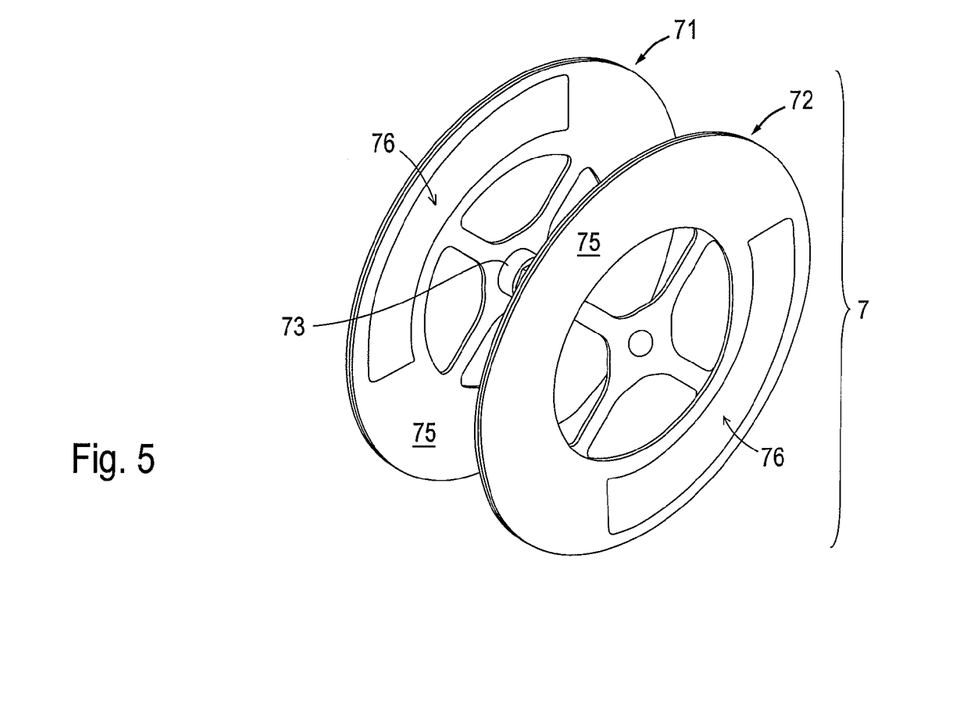
FIG. 5—shows a second embodiment of a shield, in a perspective view.

FIG. 5

In this alternative embodiment with a continuously rotating shield 7, which avoids the disadvantages of the stop-and-go operation, each element 71,72 only has one cut-out 76 whose arc is a multiple of the size of an object 8 and thus permits the latter's passage in the case of continuous movement of the shield 7. The cut-outs 76 of the two elements 71,72 are dimensioned such that they do not overlap.

Figure 8:
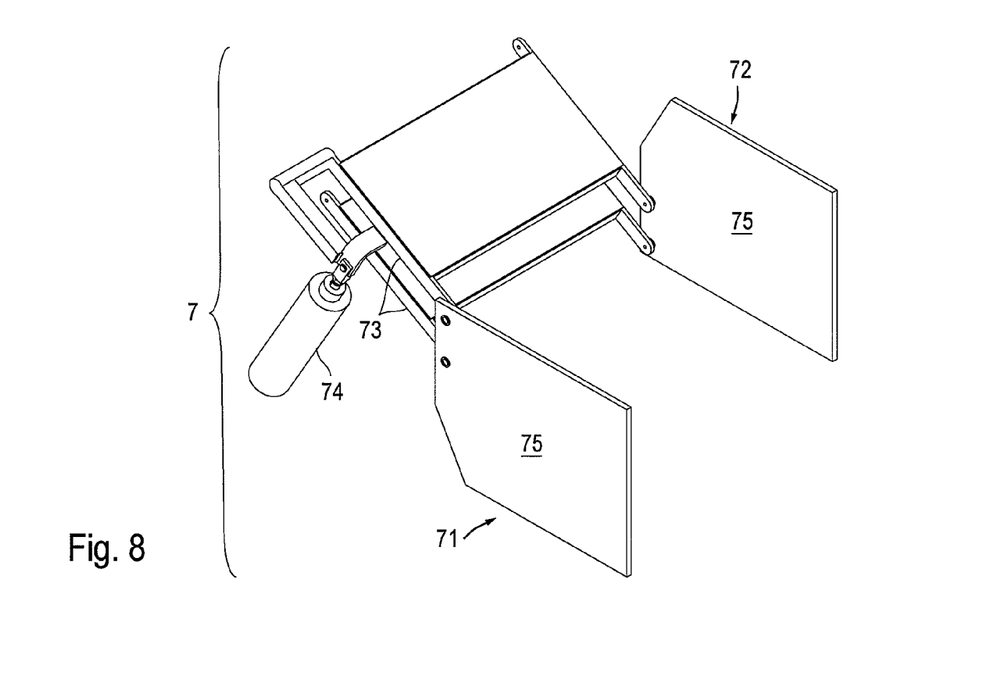
FIG. 8—shows a third embodiment of a shield, in a perspective view.

FIG. 8

The present embodiment of the shield 7 has a design which is significantly different and which is composed of two plate-shaped, displaceable or pivotable elements 71,72, between which a connection 73 extends for the coordinated movement of the two elements 71,72. This shield 7 is also connected to a drive 74, but the material region 75 extends over each element 71,72, without cut-outs 76 being present on the latter.

Figure 11:
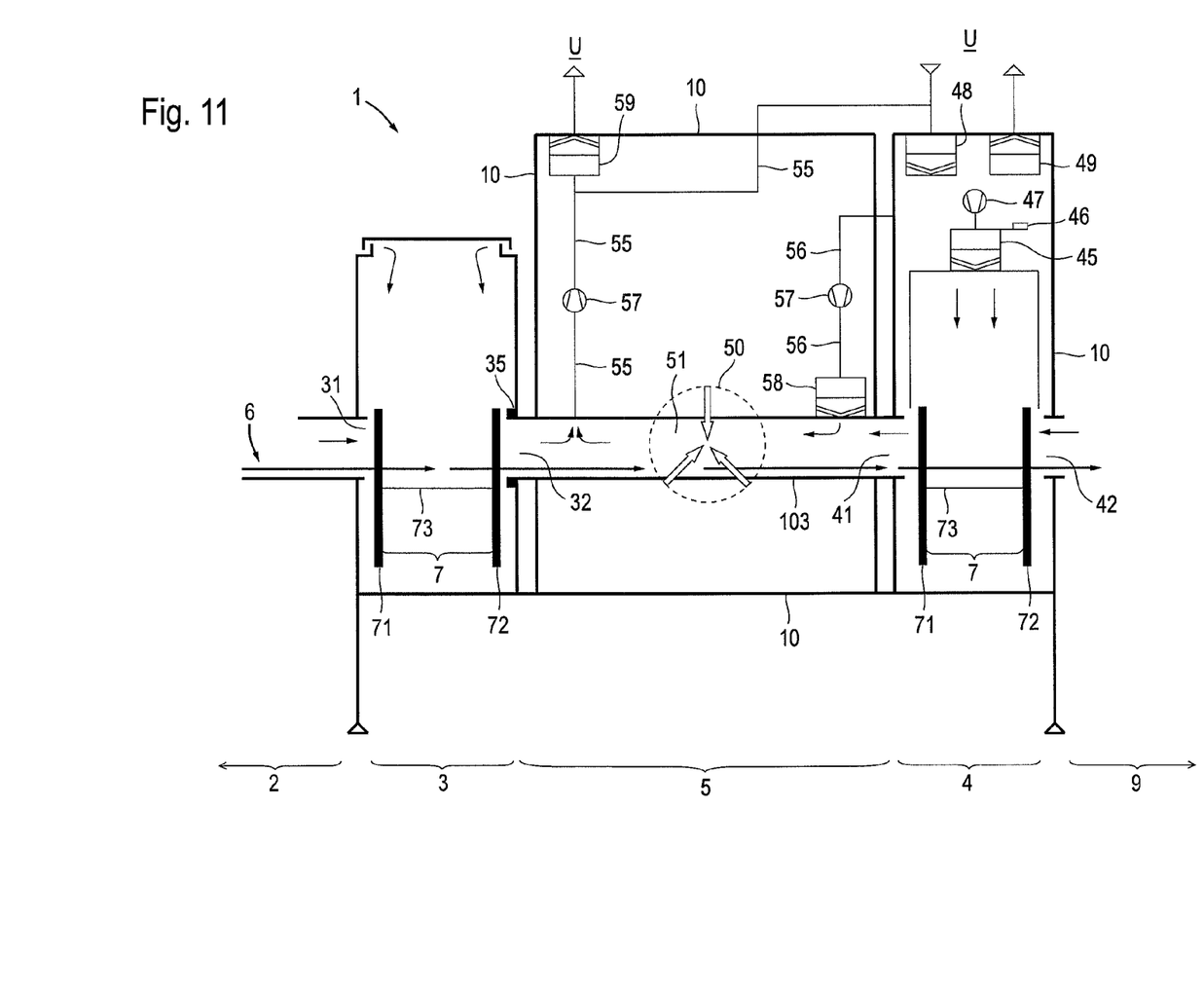
FIG. 11—shows the equipment of the installation and flow profiles occurring therein in a schematic diagram.

FIG. 11

The radiation source 50 acts into a channel 103 through which the transportation line 6 for conveying the objects 8 runs, and which channel 103 firstly extends to the second inlet opening 32 of the entry zone 3 and secondly extends to the first outlet. opening 41 of the exit zone 4. In order to achieve a qualified class of cleanliness from the radiation source 50 up to the entire exit zone 4, the latter is operated with a unidirectional air flow. To this end, an air distributor 45, in the form of a filter or a diffuser, is provided, with a ventilator 47 attached thereto. Furthermore, a conventional decontamination unit 46 is arranged within the exit zone 4. Moreover, the exit zone 4 is advantageously equipped with a feed air filter 48 and an exhaust air filter 49. A feed air filter 58 is positioned in the irradiation zone 5 between the first outlet opening 41 and the radiation source 50, which filter opens into the channel 103. A feed air line 56 extends from the feed air filter 58, and the former leads into the exit zone 4 via a ventilator 57. Feeding via the feed air filter 58 favors the unidirectional character of the flow in the exit zone 4, rinses away ozone possibly still adhering to the treated object 8, and, at the same time, dissipates the ozone created by the electron emitter 50 in the channel 103 against the direction of transportation of the objects 8. To this end, an exhaust air line 55 leaves the entry zone 3 of the channel 103 between the radiation source 50 and the second inlet opening 32. Alternatively, this exhaust air line 55 can also be led out of the entry zone 3. A filter 59 could be provided in the irradiation zone 5.

A seal 35 which can be activated is provided for locking the second inlet opening 32 in the entry zone 3, which opening forms a passage to the irradiation zone 5. This seal 35 can be mounted on a fixed installation component and, when activated, seals the second inlet opening 32 against the second element 72 of the shield 7 arranged in the entry zone 3. Alternatively, the seal 35 which can be activated is mounted on the second element 72 of the shield 7 arranged in the entry zone 3 and, when activated, seals the second inlet opening 32 against a fixed installation component. This seal is set when the decontamination phase is in operation in the exit zone 4.

In order to avoid e.g. ozone in particular, which is created when the radiation source 50 is switched on as a result of a reaction with the affected air, the treatment space within the channel 103, acted upon by the radiation source 50, is filled with an inert gas 51.

The invention claimed is:

1. An installation (1) for sterilizing objects (8) by means of a radiation source (50), with:
    a) an irradiation zone (5) in which the radiation source (50) is arranged;
    b) an entry zone (3), which is in front of the irradiation zone (5);
    c) a feed zone (2), which is in front of the entry zone (3);
    d) an exit zone (4), which adjoins the irradiation zone (5) and which is followed by a subsequent processing zone (9);
    e) a transportation line (6) which passes through the installation (1) and is used to convey the objects (8);
    f) a shield (7) which is assigned to the entry zone (3); and
    g) a shield (7) which is assigned to the exit zone (4), characterized in that
    h) the entry zone (3) has a first inlet opening (31) with a passage to the feed zone (2) and a second inlet opening (32) with a passage to the irradiation zone (5);
    i) the exit zone (4) has a first outlet opening (41) with a passage to the irradiation zone (5) and a second outlet opening (42) with a passage to the subsequent processing zone (9);
    j) the transportation line (6) extends flush through the first inlet opening (31), the second inlet opening (32), the first outlet opening (41) and the second outlet opening (42);
    k) the shields (7) are movable and in every situation with regard to position of the shields (7) in which one of the two inlet openings (31,32) or one of the two outlet openings (41,42) permits the passage of the objects (8) transported through the installation (1), the other inlet opening (32,31) and the other outlet opening (42, 41) are covered by the respectively assigned shield (7);
    l) one shield (7) is composed of two plate-shaped, displaceable or pivotable elements (71,72), a connection (73) extending between the two;
    m) the elements (71,72) have material regions (75); and
    n) the shield (7) is connected to a drive (74).

2. The installation (1) as claimed in claim 1, characterized in that
    the radiation source (50) acts into a channel (103) through which the transportation line (6) for conveying the objects (8) passes and which firstly extends to the second inlet opening (32) of the entry zone (3) and secondly extends to the first outlet opening (41) of the exit zone (4).

3. The installation (1) as claimed in claim 2, characterized in that
    a) the housing of the sterilizing installation (1) is manufactured from sandwich elements (10) which adjoin one another and are sealed off against one another;
    b) a sandwich element (10) has a radiation absorbing inner layer (100), preferably composed of lead, between two outer layers (101), preferably composed of a stainless steel plate; and
    c) a seal (102) is provided between adjacently arranged sandwich elements (10).

4. The installation (1) as claimed in claim 3, characterized in that the treatment space acted upon by the radiation source (50) is filled with an inert gas.

* * * * *